US012257415B2

(12) United States Patent
Esnault et al.

(10) Patent No.: US 12,257,415 B2
(45) Date of Patent: Mar. 25, 2025

(54) NEST FOR THE PACKAGING OF PLUNGER STOPPERS WITH INTEGRATED STACKING FEATURES ENSURING A RELIABLE ALIGNMENT OF A PILE OF NESTS

(71) Applicant: Becton Dickinson France, Le Pont-de-Claix (FR)

(72) Inventors: Gildas Esnault, Grenoble (FR); Laurent Jacquier, Saint Cassien (FR); Ferdinand Lavigne, Seyssinet-Pariset (FR); Clémentine Le Loc'h, Meylan (FR); Thomas Magguili, Vizille (FR); Cédric Rivier, Voreppe (FR)

(73) Assignee: Becton Dickinson France, Le Pont-de-Claix (FR)

( * ) Notice: Subject to any disclaimer, the term of this patent is extended or adjusted under 35 U.S.C. 154(b) by 0 days.

(21) Appl. No.: 18/274,086

(22) PCT Filed: Jan. 26, 2022

(86) PCT No.: PCT/EP2022/051748
§ 371 (c)(1),
(2) Date: Jul. 25, 2023

(87) PCT Pub. No.: WO2022/161999
PCT Pub. Date: Aug. 4, 2022

(65) Prior Publication Data
US 2024/0416029 A1    Dec. 19, 2024

(30) Foreign Application Priority Data
Jan. 26, 2021   (EP) .................................... 21305099

(51) Int. Cl.
*A61M 5/00*   (2006.01)

(52) U.S. Cl.
CPC .................................. *A61M 5/008* (2013.01)

(58) Field of Classification Search
CPC .............................. A61M 5/00; A61M 5/008
USPC ......................................... 206/364, 366, 509
See application file for complete search history.

(56) References Cited

U.S. PATENT DOCUMENTS

| 6,250,052 B1 | 6/2001 | Porfano et al. |
| 8,453,838 B2 | 6/2013 | Hill |
| 9,211,375 B2 | 12/2015 | Finke et al. |
| 9,636,680 B2 | 5/2017 | Fattinger et al. |

(Continued)

FOREIGN PATENT DOCUMENTS

| DE | 202017103606 U1 | 8/2018 |
| EP | 2436408 A1 | 4/2012 |

(Continued)

*Primary Examiner* — Bryon P Gehman
(74) *Attorney, Agent, or Firm* — The Webb Law Firm (57) ABSTRACT

A nest for the storage of medical device components, including a top surface, a bottom surface, and a plurality of receptacles for the storage of a plurality of medical device components therein. Each of the plurality of receptacles may include a sidewall portion extending downward from the bottom surface of the nest. Additionally, a plurality of ring-shaped protrusions may be provided to extend upward from the top surface of the nest and surround at least some of the plurality of receptacles. The plurality of ring-shaped protrusions may be sized and configured to receive a bottom portion of a corresponding one of the plurality of receptacles when a plurality of nests are vertically stacked relative to one another.

14 Claims, 12 Drawing Sheets

(56) References Cited

U.S. PATENT DOCUMENTS

2017/0259948 A1   9/2017  Werk et al.
2019/0135471 A1   5/2019  Barbedette et al.

FOREIGN PATENT DOCUMENTS

| EP | 2623204 A1 | 8/2013 |
| EP | 3536362 A1 | 9/2019 |
| WO | 2010062602 A1 | 6/2010 |
| WO | 2018020505 A1 | 2/2018 |

FIG.13C

NEST FOR THE PACKAGING OF PLUNGER STOPPERS WITH INTEGRATED STACKING FEATURES ENSURING A RELIABLE ALIGNMENT OF A PILE OF NESTS

CROSS-REFERENCE TO RELATED APPLICATIONS

This application is the United States national phase of International Application No. PCT/EP2022/051748 filed Jan. 26, 2022, and claims priority to European priority application EP 21305099.0, entitled "A Nest for the Packaging of Plunger Stoppers with Integrated Stacking Features Ensuring a Reliable Alignment of a Pile of Nests", filed Jan. 26, 2021, the entire disclosures of which are hereby incorporated by reference in their entirety.

BACKGROUND

Field of the Disclosure

The present disclosure relates generally to nest arrangements for the packaging of plunger stoppers used in medical devices such as, e.g., syringes. More particularly, the present disclosure relates to nest arrangements utilizing various integrated stacking features so as to ensure reliable alignment of a pile (or stack) of nests positioned vertically atop one another.

Description of the Related Art

As is known in the art, transfer or storage devices for delivery or storage of a medicament, drug, or vaccine (such as, e.g., syringes) utilize a plunger stopper in contact with an inside surface of a generally tubular syringe barrel in order to draw a substance into (or expel a substance from) the device by way of a plunger rod.

Currently, many such devices are filled and assembled using automated filling machines. Not only do such machines improve productivity and accuracy, but they also provide for a substantially sterile and aseptic filling environment. The various components of the devices (e.g., plunger stoppers, syringe barrels, etc.) are separately provided within the filling machines to enable at least some level of automated assembly.

Typically, a plurality of plunger stoppers are provided in bags or in nests (which are also provided in bags) to be accessed by the filling machine during assembly. Conversely, the syringe barrels are generally packaged in nests having numerous "chimneys" formed therein to hold the barrels, with each nest configured to be held within a tub when introduced into the filling machine.

While the current nests for syringe barrels are specifically designed for use with tubs, the current nests designed for holding plunger stoppers are not configured for use with a specific tub profile, nor do they fit securely within the tubs used for syringe barrels. In some automated filling machines, the lack of a tub for holding the nests of plunger stoppers does not present an issue. However, in other, more recently-designed filling equipment (such as, e.g., the Vanrx SA25robotic aseptic filling workcell from Vanrx Pharmasystems Inc.), only components packaged in both nests and tubs are capable of being handled.

Furthermore, as noted above, currently-available nests for plunger stoppers are not designed to be held within existing tub designs, nor are their nests configured for plunger stoppers which are consistently stackable. Thus, if one were to attempt to utilize existing nests and tubs together in relation to plunger stoppers, the combination may result in unreliable positioning and unwanted movement of the nests within the tub and/or relative to nests above or below when stacked, which would be problematic for the robotic handling of the nests within the filling equipment. Documents DE202017103606U1, WO2010062602A1, WO2018020505A1, US2017259948A1 and EP2436408A1 relate to packaging for containers.

SUMMARY

In view of the foregoing, there exists a need for a nest designed specifically for plunger stoppers, as well as a nest designed to ensure consistent and secure alignment of nests when vertically stacked either within or outside of a tub.

Embodiments of the present disclosure are directed to a nest for the storage of medical device components. The nest may include a top surface, a bottom surface, and a plurality of receptacles for the storage of a plurality of medical device components therein. Each of the plurality of receptacles includes a sidewall portion extending downward from the bottom surface of the nest. The nest may also include a plurality of ring-shaped protrusions extending upward from the top surface of the nest and surrounding at least some of the plurality of receptacles. Each of the plurality of ring-shaped protrusions may be sized and configured to receive a bottom portion of a corresponding one of the plurality of receptacles when a plurality of nests are vertically stacked relative to one another.

In some embodiments, the ring-shaped protrusions may surround each of the plurality of receptacles.

In some embodiments, the ring-shaped protrusions surround fewer than all of the plurality of receptacles.

In some embodiments, the plurality of receptacles are substantially frustoconical in shape.

In some embodiments, the nest further includes a ledge portion surrounding an upper opening of each of the receptacles.

In some embodiments, the ledge portion is sized so as to support a bottom surface of a respective one of the plurality of receptacles.

In some embodiments, a width of each ledge portion is about 1.5 mm.

In some embodiments, the height of each of the plurality of ring-shaped protrusions extending above the top surface of the nest is between 1.0-2.0 mm.

In some embodiments, an upper surface (23) of each of the ring-shaped protrusions is rounded or chamfered.

In some embodiments the sidewall portion of a first set of the plurality of receptacles extends farther downward from the bottom surface of the nest than the sidewall portion of a second set of the plurality of receptacles.

In some embodiments, each of the plurality of receptacles having the sidewall portion which extends farther downward from the bottom surface of the nest than the sidewall portion of a second set of the plurality of receptacles is surrounded by one of the plurality of ring-shaped protrusions.

In some embodiments, the nest further includes at least one finger opening formed therein.

In some embodiments, the nest further includes a flange extending at least partially around each finger opening and extending from the bottom surface of the nest.

In some embodiments, the plurality of receptacles include between 100-160 receptacles.

In some embodiments the nest is formed of polypropylene.

Further details and advantages of the present disclosure will be understood from the following detailed description read in conjunction with the accompanying drawings.

DESCRIPTION OF THE INVENTION

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For the purposes of the description hereinafter, the terms "upper", "lower", "right", "left", "vertical", "horizontal", "top", "bottom", "lateral", "longitudinal", and derivatives thereof shall relate to the invention as it is oriented in the drawings. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

Figure 1:
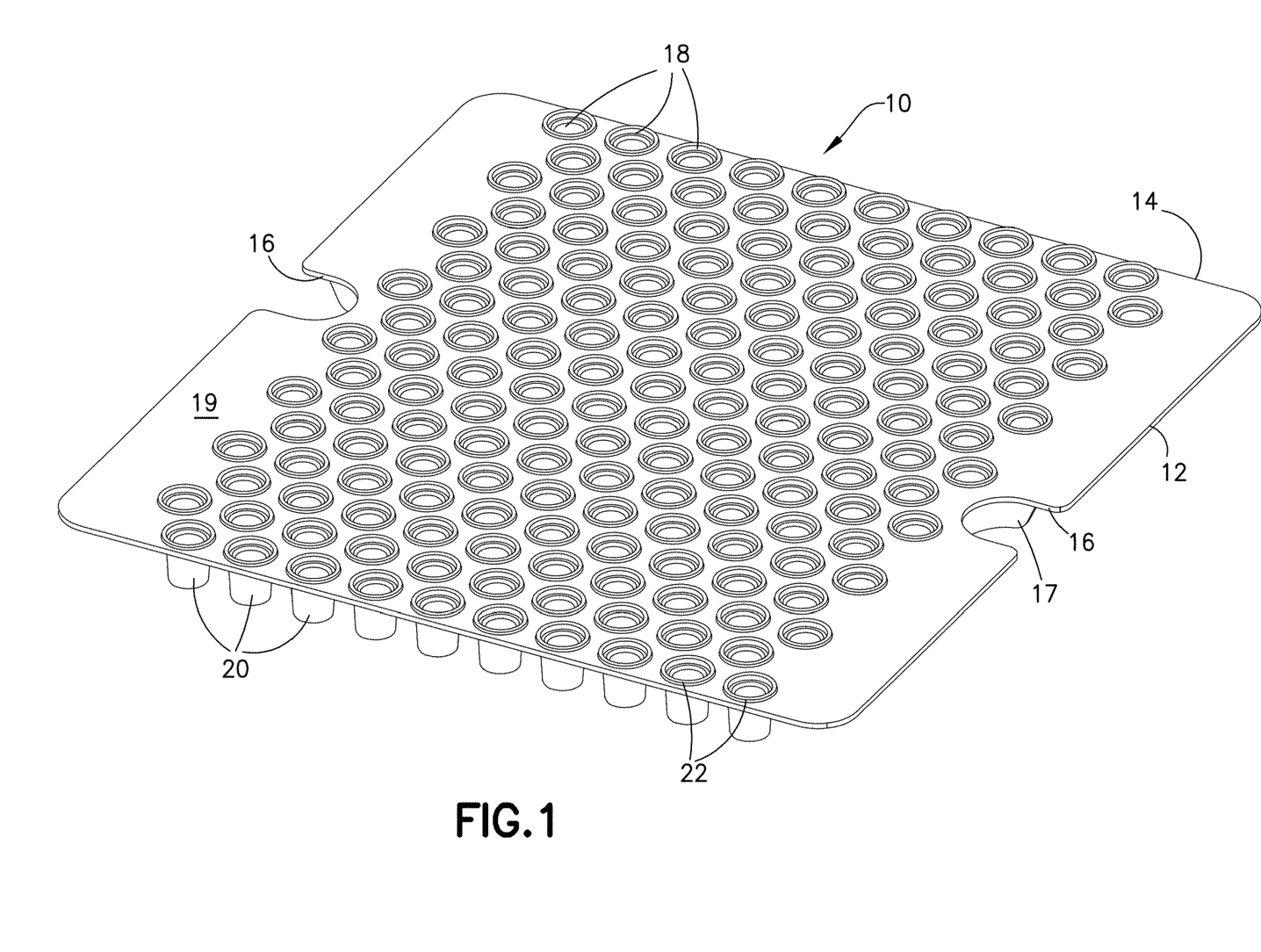
FIG. 1 is a top isometric view of a nest for the storage of plunger stoppers in accordance with an aspect of the present disclosure.
Figure 2:
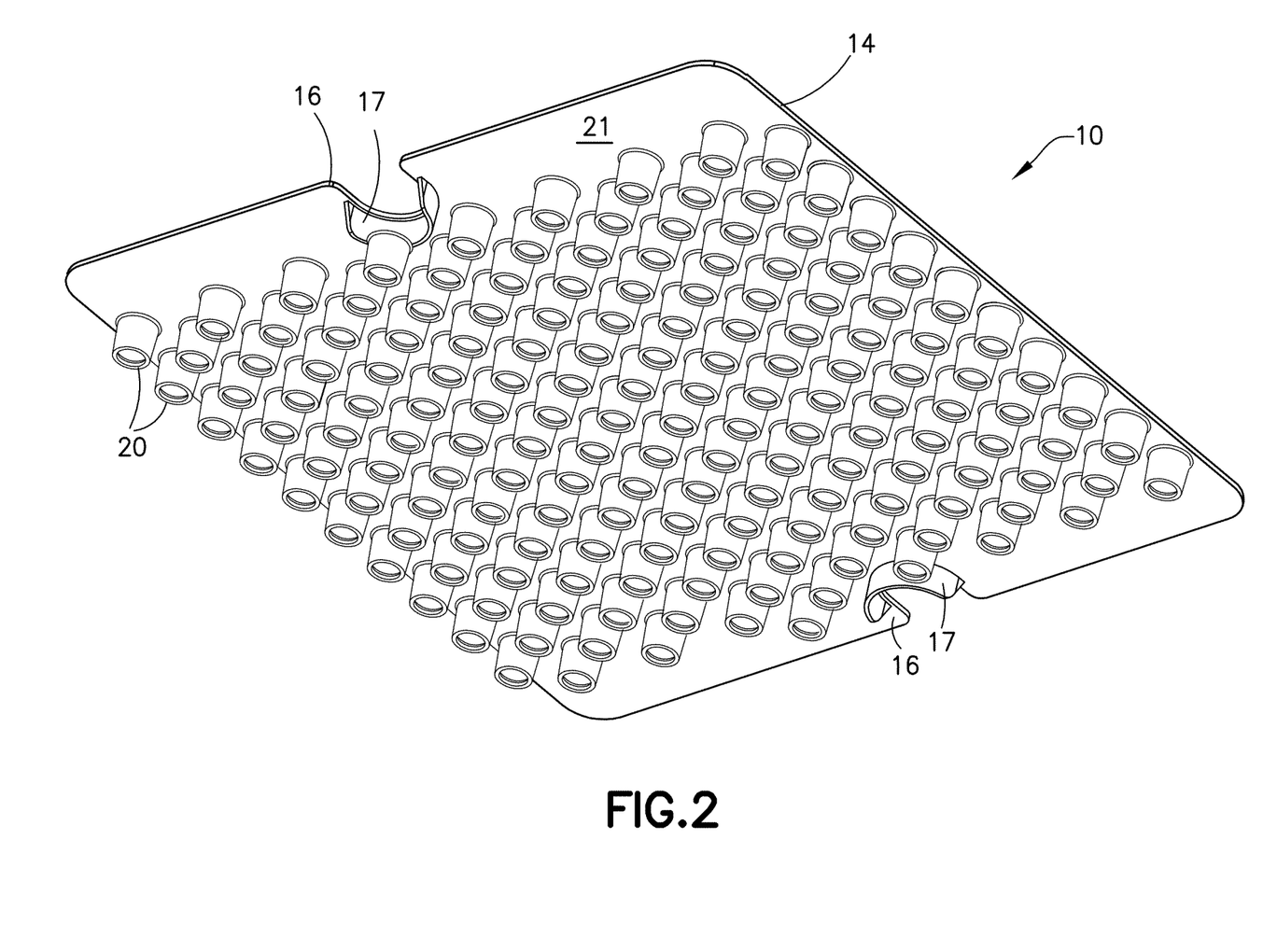
FIG. 2 is a bottom isometric view of the nest of FIG. 1.
Figure 3:
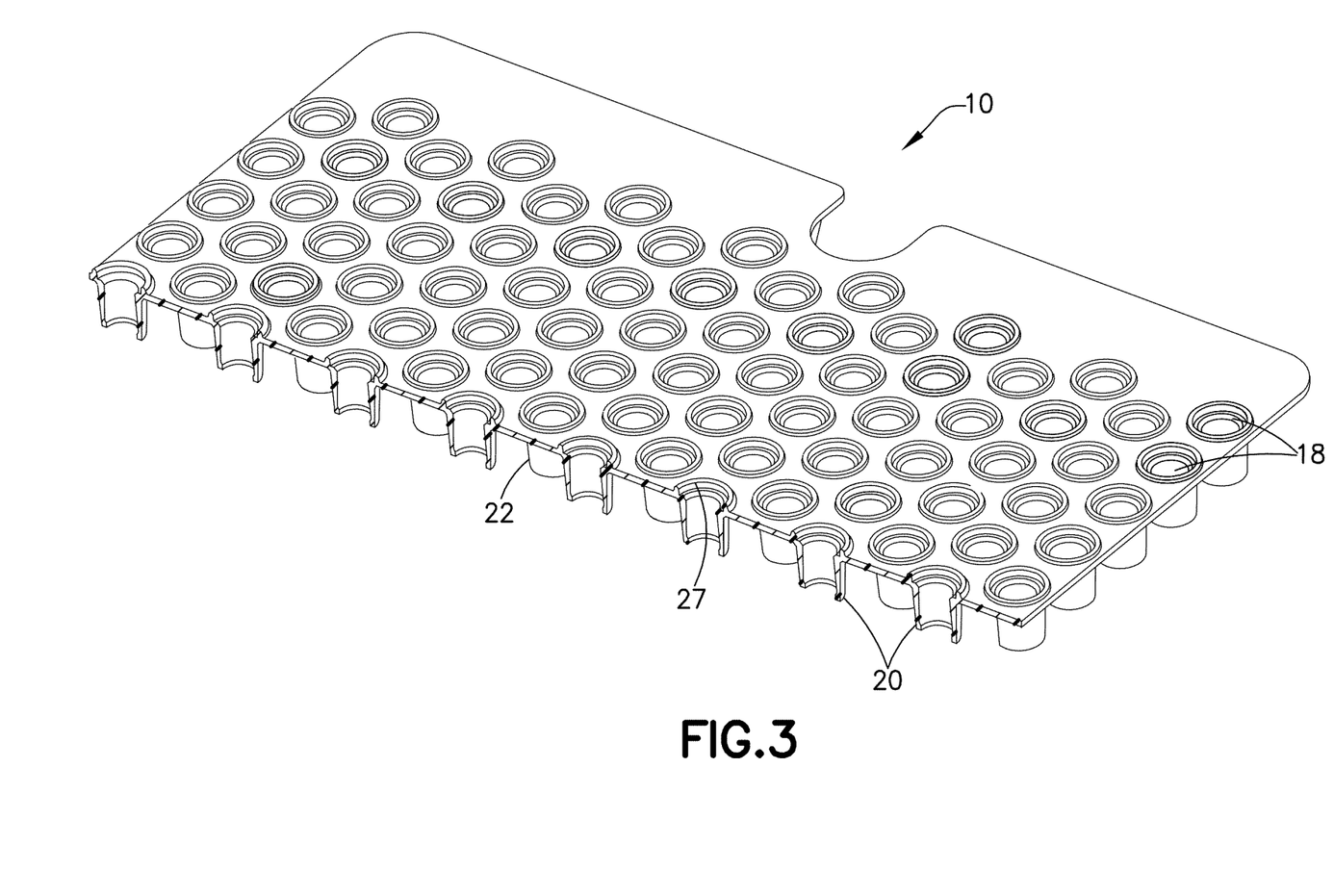
FIG. 3 is a cross-sectional isometric view of the nest of FIG. 1.

Referring to FIGS. 1 and 2, a nest 10 in accordance with an aspect of the present disclosure is shown. Each nest 10 is configured to store a plurality of plunger stoppers (not shown) in a way that provides for desired positioning and alignment of both the plunger stoppers and nest(s) to allow for accurate handling by the robotic components of the automated filling machines. While not shown, a plurality of nests 10 are capable of being removably retained within a tub or other holding arrangement, with the nests 10 configured to be stackable vertically atop one another, as will be described in further detail below. Typically, between two and ten nests may be stacked onto each other. For example, at least two nests are stacked onto each other. Additionally, it is to be understood that the nests described in the present disclosure are not limited to use with plunger stoppers, and may be utilized with other elements and/or devices, such as, e.g., needle covers, tip caps, or any other medical components.

Figure 4:
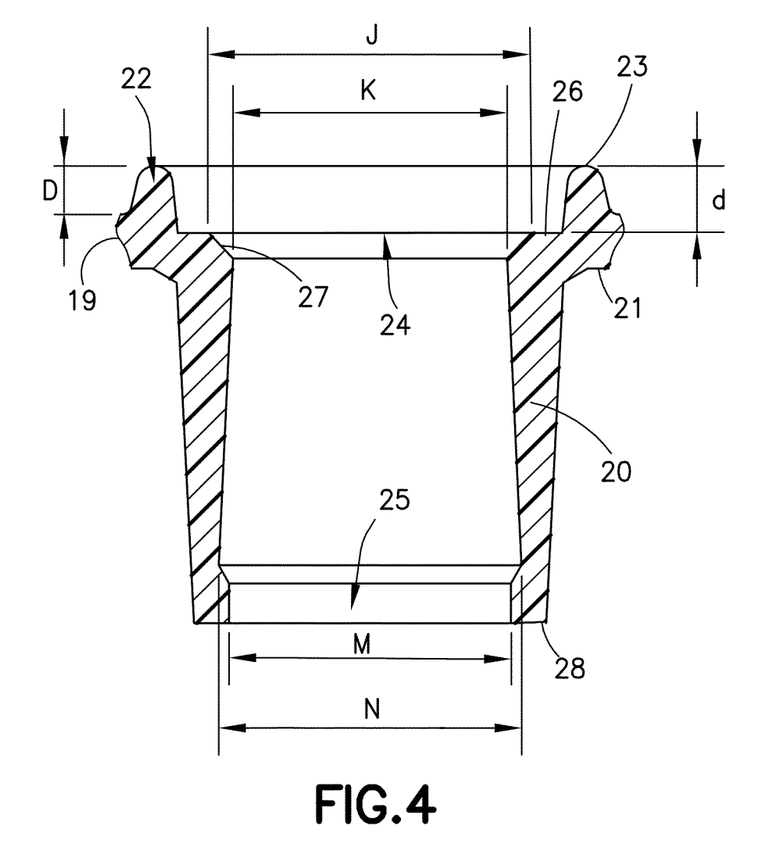
FIG. 4 is a cross-sectional side view of a stopper receptacle of the nest of FIG. 1.

Specifically, each nest 10 includes a plurality of stopper receptacles 18 formed therein. The stopper receptacles 18 may be formed as substantially frustoconical "chimneys", each capable of holding a plunger stopper therein for access and removal by components of an autonomous filling machine. Referring to FIG. 4, each stopper receptacle 18 includes an upper opening 24 formed in a top surface 19 of the nest 10, while the "chimney" of the stopper receptacle 18 is formed by a frustoconical wall portion 20 which extends below a bottom surface 21 of the nest 10. The diameter and size of each stopper receptacle 18 may vary based on the type of stopper utilized during a particular filling operation. In one embodiment, the nest 10 may be configured to retain, e.g., 160 stoppers sized for use in a 1 mL syringe. However, it is to be understood that the nest 10 may be configured to hold more or fewer stoppers, as well as stoppers of differing size(s). For example, a nest in accordance with another embodiment may be configured to hold 100 stoppers sized for use with a 2.25 ml syringe. Thus, in some embodiments, the overall number and positioning of stopper receptacles 18 may vary as compared to that which is shown in FIGS. 1 and 2. Additionally, while not shown, it is to be understood that one or more ribs may extend along at least a portion of the frustoconical wall portion 20 so as to provide further reinforcement of the stopper receptacle 18 relative to the bottom surface 21 of the nest 10.

The nest 10 includes a pair of long sides 12 and a pair of short sides 14. However, in alternative embodiments, it is to be understood that the sides of nest 10 need not be different in length and/or parallel, and may instead be, e.g., equal, non-parallel, etc. The general dimensions of each nest 10 (i.e., length, width, and height) may be adapted based on the specific holding tub or automated filling machine being utilized.

As shown in FIGS. 1 and 2, the long sides 12 may each include a finger opening 16 formed thereon, wherein each finger opening 16 is designed to enable simplified manual loading (and/or removal) of the nest 10 into (or from), e.g., a tub or other holding arrangement. In some embodiments, a flange 17 may at least partially surround each finger opening 16 and extend from the bottom surface 21 of nest 10, thereby providing the user with a larger surface area upon which to grip the nest 10. While two finger openings 16 are shown on opposing long sides 12 in FIGS. 1 and 2, it is to be understood that nest 10 may include more or fewer finger openings, either on long sides 12 or the short sides 14. Additionally, in some embodiments, the finger openings 16 may be omitted altogether.

Referring to FIGS. 1-4, each stopper receptacle 18 of nest 10 further includes a ring-shaped protrusion 22 formed substantially around the upper opening 24 and extending above the top surface 19. As will be described in further detail below, the ring-shaped protrusions 22 are configured to aid in the relative alignment of nests 10 if and when they are stacked atop one another, while further providing for limited lateral movement (or "play") of nests 10 with respect to one another. The ring-shaped protrusions 22 are sized and configured so as to resist the dislodgement of stacked nests 10 due to only minimal lateral forces applied to the nests 10, but still allow for the vertical separation of nests 10 when desired.

In the embodiment illustrated in FIGS. 1-4, the ring-shaped protrusions 22 are provided around each stopper receptacle 18 of the nest 10. However, in alternative embodiments, it is to be understood that ring-shaped protrusions 22 may be provided around fewer than all stopper receptacles 18. Additionally, while ring-shaped protrusions 22 are illustrated as extending a full 360° around the stopper receptacle 18, it is to be understood that the protrusions need not fully extend around stopper receptacle 18. That is, in some embodiments, the protrusions 22 may be broken at one or more locations surrounding the upper opening 24 such that less than a full 360° of protruding surface is provided around the stopper receptacle 18.

Referring to FIG. 4, a cross-sectional view of a stopper receptacle 18 in accordance with an aspect of the present disclosure is shown. As described above, a ring-shaped protrusion 22 surrounds the upper opening 24 of stopper receptacle 18, while frustoconical wall portion 20 extends below the bottom surface 21. In one embodiment, the upper opening 24 may have a diameter K of, e.g., between 6-9 mm, with the diameter of the upper opening 24 (and overall size of the stopper receptacle 18) being dependent upon the size of the stopper to be stored therein. A lower opening 25 may be formed in the bottom portion of the stopper receptacle 18, with the lower opening 25 being bound by a bottom surface 28 of the stopper receptacle 18. In one embodiment, the lower opening 25 may have a diameter M, where diameter M is substantially equal to diameter K of the upper opening 24 (e.g., between 6-9 mm). Thus, it is to be understood that upper opening 24 is configured to have substantially the same diameter as the lower opening 25, thereby allowing a stopper to be inserted into the stopper receptacle 18 via the upper opening 24, while also allowing the stopper to be removed from the stopper receptacle 18 via the lower opening 25. The stopper receptacle 18 may be internally formed such that its largest internal diameter N is larger than both the diameter K of the upper opening 24 and the diameter M of the lower opening 25. In this way, the deformable stopper (not shown) may be pressed, by force, through both upper opening 24 and lower opening 25, but may expand for storage within the stopper receptacle 18.

The stopper receptacle 18 may also include a ledge portion 26 surrounding the upper opening 24. The ledge portion 26, in the form of an annulus, provides for a substantially flat support surface upon which the bottom surface 28 of a stopper receptacle 18 of a separate nest 10 may rest when one or more nests 10 are vertically stacked relative to one another. If a ring-shaped protrusion 22 is present, the ledge portion 26 may be located interior to the ring-shaped protrusion 22. In one embodiment, the width of the ledge portion 26 may be, e.g., about 1.5 mm, thereby providing an adequate support surface for the bottom surface 28 of an adjacent stopper receptacle 18, while also providing for limited lateral movement (i.e., "play") of an adjacent stopper receptacle 18, which allows for selective separation of stacked nests 10 from one another. It is to be understood that the width of the ledge portion 26 may be varied based on the size of the stopper receptacle 18, the number of stopper receptacles 18, etc. Additionally, the stopper receptacle 18 may include a chamfered edge 27 between the ledge portion 26 and the frustoconical wall portion 20. This chamfered edge 27 may have an outside diameter J which is larger than the diameter K of the upper opening 24, thereby providing for easier insertion of a stopper (not shown) into the stopper receptacle 18.

Referring still to FIG. 4, the ring-shaped protrusion 22 is configured to extend above the top surface 19 of the nest 10 so as to substantially prevent easy dislodgement of adjacently stacked nests upon the application of minimal lateral force on a vertical stack of nests. For example, in one embodiment, the ring-shaped protrusion 22 may extend a depth D of about 1.5 mm from an upper portion 23 to the ledge portion 26, and may extend a height d of about at least 1.0 mm from the upper portion 23 to the top surface 19 of the nest 10. In this way, the depth/height of the ring-shaped protrusion 22 is sufficient so as to prevent easy dislodgement of adjacently stacked nests, while also absorbing both the nest's natural deformation and vertical movement due to, e.g., material properties, overall nest length and width, vibrations during transport, etc. Furthermore, in some embodiments, the upper portion 23 of the ring-shaped protrusion may be rounded or chamfered so as to enable smooth insertion of adjacent stopper receptacles 18 when a plurality of nests are stacked upon one another.

Each nest 10 may be formed of any suitable material, and via any suitable method. For example, nest 10 may be formed of, e.g., a plastic, polymer (e.g., polypropylene), metal, etc., and may be formed by, e.g., molding, stamping, extrusion, welding, etc. Furthermore, nest 10 may be formed as a single piece, or as multiple pieces coupled together. If formed of multiple pieces, the materials forming each piece may be the same or different.

Next, referring to FIGS. 5-8, a nest 30 in accordance with another aspect of the present disclosure is illustrated. Similar to nest 10 described above with respect to FIGS. 1-4, nest 30 is configured to store a plurality of plunger stoppers (not shown) in a way that provides for desired positioning and alignment of both the plunger stoppers and nest(s) to allow for accurate handling by the robotic components of the automated filling machines. Each nest 30 is configured to be vertically stackable upon another nest 30, as will be described in further detail below.

The nest 30 includes a plurality of stopper receptacles 36, 37 formed therein. Unlike the stopper receptacles 18 described above with respect to FIGS. 1-4, which are uniform in size, stopper receptacles 36, 37 are dissimilar in size. That is, stopper receptacles 36 each include a "chimney" formed by a frustoconical wall portion 40 which extends below a bottom surface 39 of the nest 30 by a first distance. On the other hand, the stopper receptacles 37 include a frustoconical wall portion 41 which extends below a bottom surface 39 of the nest 30 by a second distance, with the second distance being slightly longer than the first distance. As will be described below, this variation in size of the stopper receptacles 37 aids in consistent alignment and retention of nests 30 when vertically stacked upon each other.

The diameter and size of each stopper receptacles 36, 37 may vary based on the type of stopper utilized during a particular filling operation. However, while the length of frustoconical wall portions 40, 41 relative to the bottom surface 39 may be different, it is to be understood that the stopper receptacles 36, 37 are not intended to hold stoppers that are different in size. In one embodiment, the nest 30 may be configured to retain, e.g., 100 stoppers sized for use in a 1-3 mL syringe. However, it is to be understood that the nest 30 may be configured to hold more or fewer stoppers, as well as stoppers of differing size(s). Thus, in some embodiments, the overall number and positioning of stopper receptacles 36, 37 may also vary as compared to that which is shown in FIGS. 5-8. Additionally, while not shown, it is to be understood that one or more ribs may extend along at least a portion of the frustoconical wall portions 40, 41 so as to provide further reinforcement of the stopper receptacles 36, 37 relative to the bottom surface 39 of the nest 30. The number of ribs may be determined based on the desired rigidity of stopper receptacles 36, 37.

The nest 30 may include a pair of long sides 32 and a pair of short sides 33. However, in alternative embodiments, it is to be understood that the sides of nest 30 need not be different in length and/or parallel, and may instead be, e.g., equal, non-parallel, etc. The general dimensions of each nest 30 (i.e., length, width, and height) may be adapted based on the specific automated filling machine being utilized.

Figure 5:
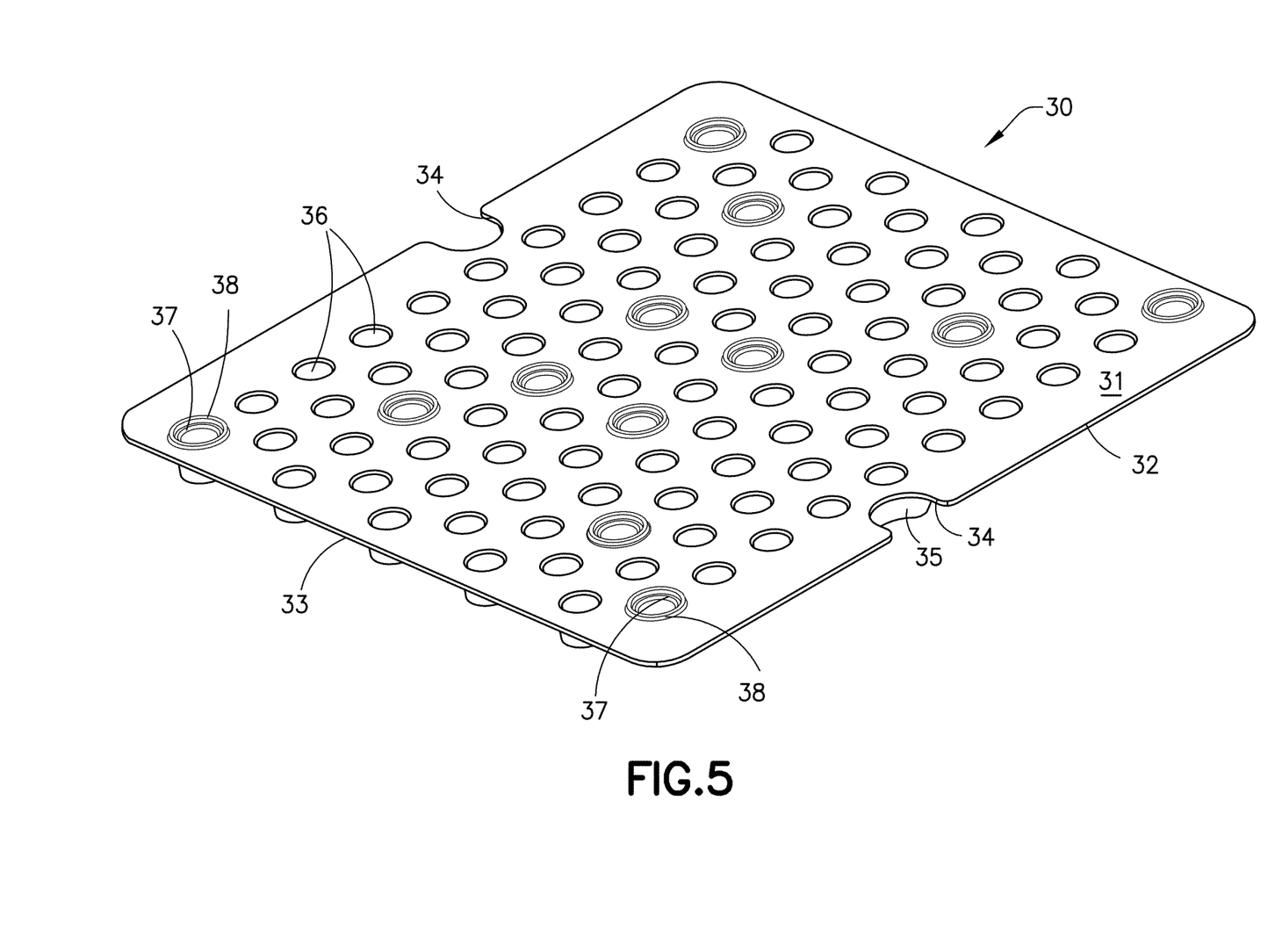
FIG. 5 is a top isometric view of a nest for the storage of plunger stoppers in accordance with another aspect of the present disclosure.
Figure 6:
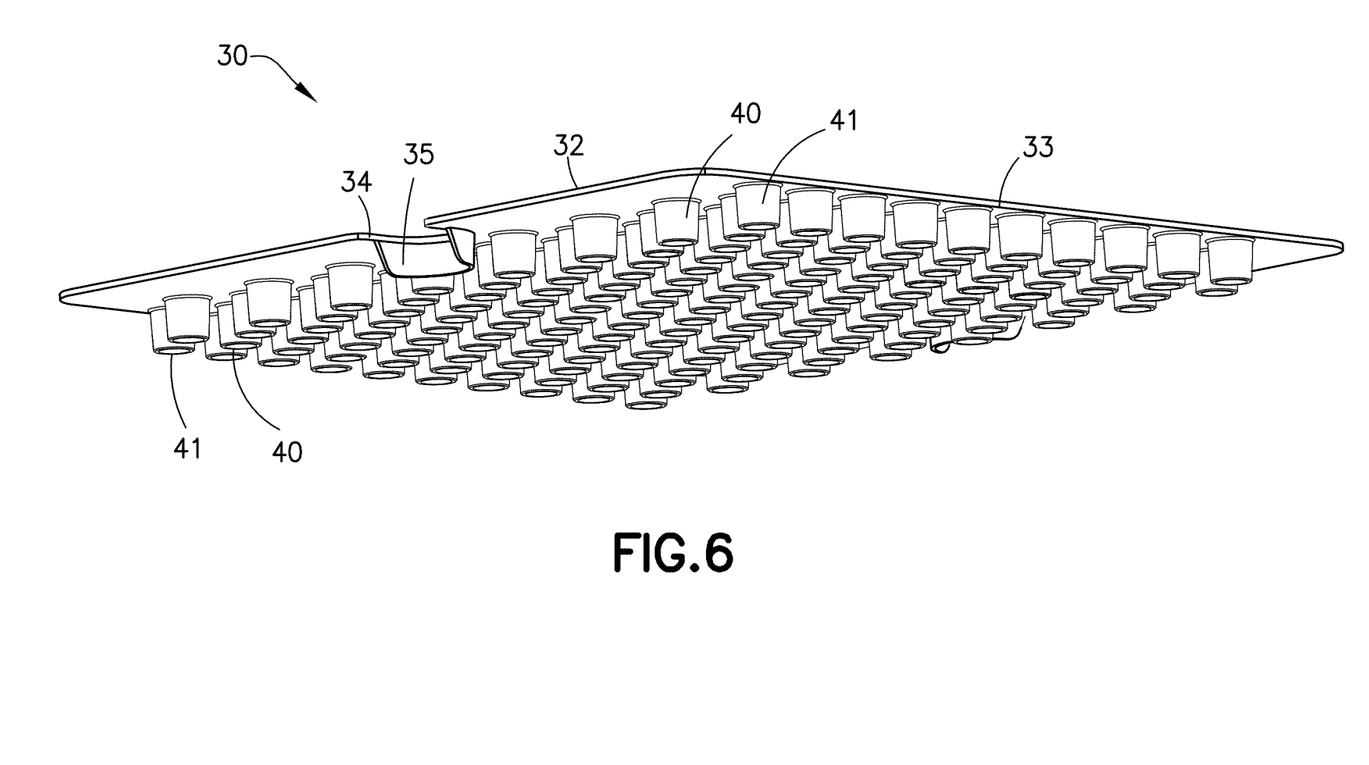
FIG. 6 is a bottom isometric view of the nest of FIG. 5.
Figure 7:
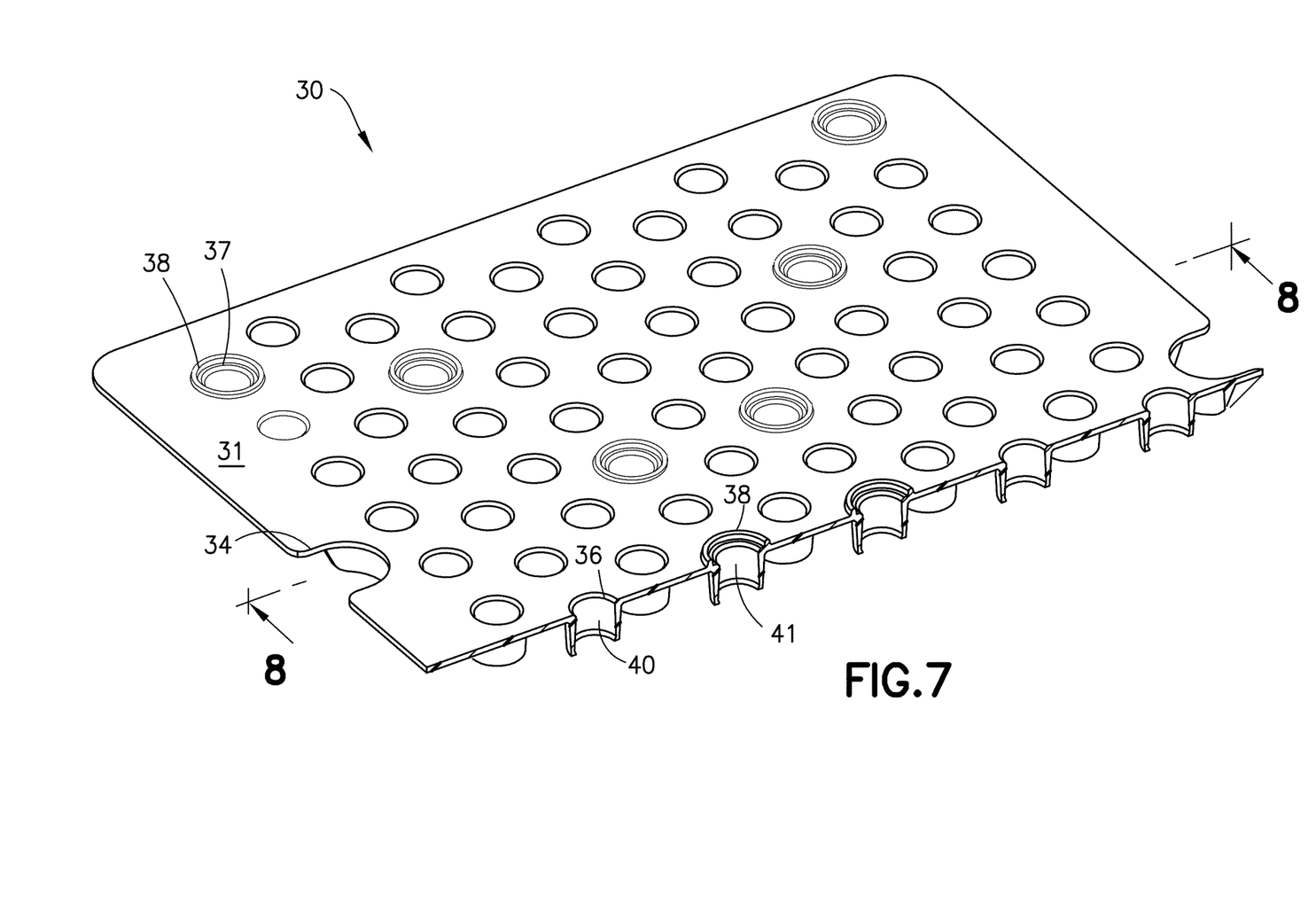
FIG. 7 is a cross-sectional isometric view of the nest of FIG. 5.

As shown in FIGS. 5 and 6, the long sides 32 may each include a finger opening 34 formed thereon, wherein each finger opening 34 is designed to enable simplified manual loading (and/or removal) of the nest 30 into (or from), e.g., a tub or other holding arrangement. In some embodiments, a flange 35 may at least partially surround each finger opening 34 and extend from the bottom surface 39 of nest 30, thereby providing the user with a larger surface area upon which to grip the nest 30. While two finger openings 34 are shown on opposing long sides 32 in FIGS. 5 and 6, it is to be understood that nest 30 may include more or fewer finger openings, either on long sides 32 or the short sides 33. Additionally, in some embodiments, the finger openings 34 may be omitted altogether.

Referring still to FIGS. 5-8, each stopper receptacle 37 of nest 30 further includes a ring-shaped protrusion 38 formed substantially around an upper opening and extending above the top surface 31 of the nest 30. Similar to ring-shaped protrusions 22 described above with respect to FIGS. 1-4, ring-shaped protrusions 38 are configured to aid in the relative alignment of nests 30 if and when they are stacked atop one another, while further providing for limited lateral movement (or "play") of nests 30 with respect to one another. However, unlike the embodiment shown in FIGS. 1-4, ring-shaped protrusions 38 are only provided around stopper receptacles 37, and not stopper receptacles 36. Thus, only a selected subset of stopper receptacles are provided with the ring-shaped protrusions 38, which may simplify manufacturing of the nest 30, while still providing for the desired alignment of stacked nests. In the embodiment shown in FIG. 5, a total of twelve dispersed ring-shaped protrusions 38 (and, thus, twelve stopper receptacles 37) are shown. However, it is to be understood that more or fewer ring-shaped protrusions 38 and/or stopper receptacles 37, at varying positions, may be provided. The number and location of the ring-shaped protrusions 38 may be adapted and/or optimized based on possible deformation of the nest 30 due to, e.g., molding. For example, as shown in FIG. 5, the rings-shaped protrusions 38 are located a central portion, intermediate portions, and the respective corners of the nest 30. In this way, the spaced-apart ring-shaped protrusions 38 may be positioned so as to provide desired alignment of the nests even if deformation occurs during manufacturing, transport, etc.

Additionally, while ring-shaped protrusions 38 are illustrated as extending a full 360° around the stopper receptacle 37, it is to be understood that the protrusions need not fully extend around stopper receptacle 37. That is, in some embodiments, the protrusions 38 may be broken at one or more locations surrounding the upper opening such that less than a full 360° of protruding surface is provided around the stopper receptacle 37.

Figure 8:
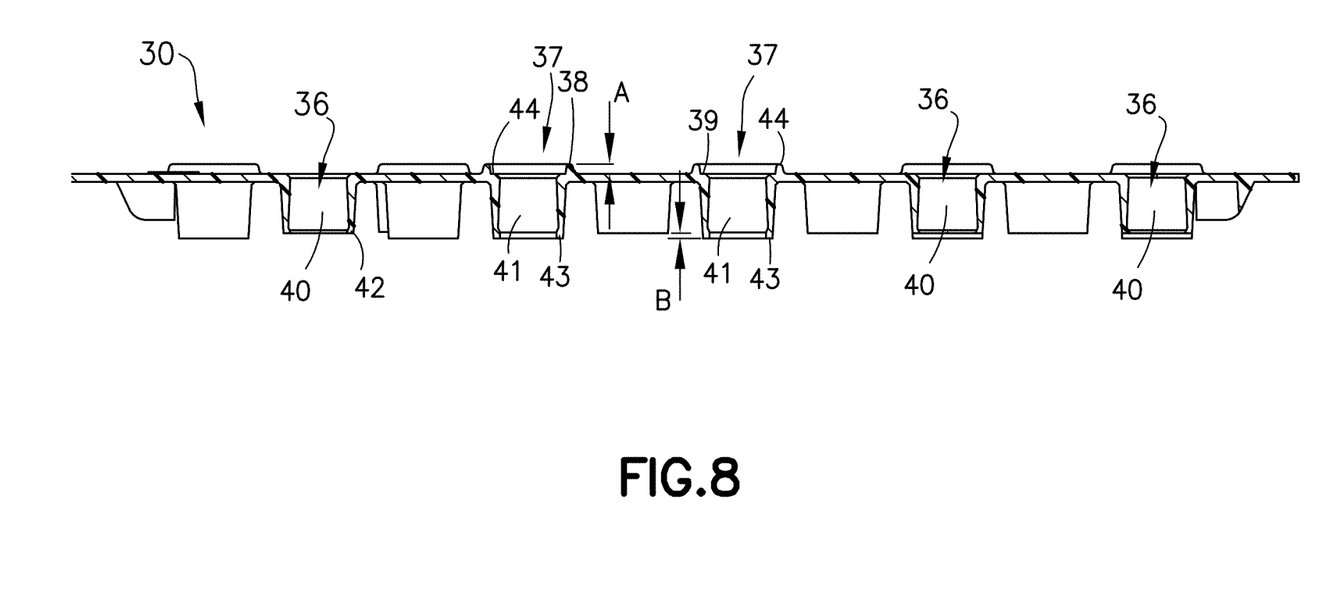
FIG. 8 is a cross-sectional side view of the nest of FIG. 5.

Referring to FIG. 8, a cross-sectional view of nest 30 is shown. Each stopper receptacle 37 further includes a ledge portion 44. The ledge portion 44, in the form of an annulus, is located interior to the ring-shaped protrusion 38 and provides for a substantially flat support surface upon which the bottom surface 43 of a stopper receptacle 37 of a separate nest 30 may rest when one or more nests 30 are vertically stacked relative to one another. In one embodiment, the width of the ledge portion 44 may be, e.g., about 1.5 mm, thereby providing an adequate support surface for the bottom surface 43 of an adjacent stopper receptacle 37, while also providing for limited lateral movement (i.e., "play") of an adjacent stopper receptacle 37, which allows for selective separation of stacked nests 30 from one another. It is to be understood that the width of the ledge portion 44 may be varied based on the size of the stopper receptacle 37, the number of stopper receptacles 37, etc.

The ring-shaped protrusion 38 is configured to extend above the top surface 31 of the nest 30 so as to substantially prevent easy dislodgement of adjacently stacked nests upon the application of minimal lateral force on a vertical stack of nests. For example, in one embodiment, the ring-shaped protrusion 38 may extend a height A of about 1.5-2.0 mm (and preferably between 1.5-1.6 mm) above the top surface 31. In this way, the depth/height of the ring-shaped protrusion 38 is sufficient so as to prevent easy dislodgement of adjacently stacked nests, while also absorbing both the nest's natural deformation and vertical movement due to, e.g., material properties, overall nest length and width, etc. Furthermore, in some embodiments, the ring-shaped protrusion 38 may be rounded or chamfered so as to enable smooth insertion of adjacent stopper receptacles 37 when a plurality of nests are stacked upon one another.

Referring still to FIG. 8, and as described above, the length of the frustoconical wall portion 41 that extends below the bottom surface 39 of nest 30 is slightly longer than the length of the frustoconical wall portion 40 that extends below the bottom surface 39. For example, the distance B from the bottom surface 42 of the frustoconical wall portion 40 to the bottom surface 43 of the frustoconical wall portion 41 may be between 0.5-1 mm. With this difference in the length, the stopper receptacles 37 of adjacently stacked nests 30 are more easily aligned with the ring-shaped protrusions 38, thereby providing for consistent alignment between vertically-stacked nests 30 via only a subset of the overall number of stopper receptacles.

Each nest 30 may be formed of any suitable material, and via any suitable method. For example, nest 30 may be formed of, e.g., a plastic, polymer (e.g., polypropylene), metal, etc., and may be formed by, e.g., molding, stamping, extrusion, welding, etc. Furthermore, nest 30 may be formed as a single piece, or as multiple pieces coupled together. If formed of multiple pieces, the materials forming each piece may be the same or different.

Furthermore, while FIGS. 5-8 illustrate a nest 30 having a plurality of spaced-apart ring-shaped protrusions 38, it is to be understood that other embodiments in accordance with the present disclosure may omit the ring-shaped protrusions entirely. That is, a nest in accordance with another embodiment may include the stopper receptacles 36, 37 having differing sizes, the nest may rely on other aspects or features (e.g., ledge portions 44, chamfered portions, etc.) in order to provide for the desired alignment (and to prevent unintended dislodgement) of vertically-stacked nests.

Next, referring to FIGS. 9-12, a nest 50 in accordance with another aspect of the present disclosure is illustrated. Similar to nests described in relation to FIGS. 1-8 above, nest 50 is configured to store a plurality of plunger stoppers (not shown) in a way that provides for desired positioning and alignment of both the plunger stoppers and nest(s) to allow for accurate handling by the robotic components of the automated filling machines. Each nest 50 is configured to be vertically stackable upon another nest 50, as will be described in further detail below.

Each nest 50 includes a plurality of stopper receptacles 56 formed therein. The stopper receptacles 56 may be formed as substantially frustoconical "chimneys", each capable of holding a plunger stopper therein for access and removal by components of an autonomous filling machine. Each stopper receptacle 56 includes an upper opening formed in a top surface 51 of the nest 50, while the "chimney" of the stopper receptacle 56 is formed by a frustoconical wall portion 58 which extends below a bottom surface 59 of the nest 50. The diameter and size of each stopper receptacle 56 may vary based on the type of stopper utilized during a particular filling operation.

The nest 50 includes a pair of long sides 52 and a pair of short sides 53. However, in alternative embodiments, it is to be understood that the sides of nest 50 need not be different in length and/or parallel, and may instead be, e.g., equal, non-parallel, etc. The general dimensions of each nest 50 (i.e., length, width, and height) may be adapted based on the specific automated filling machine being utilized.

Figure 9:
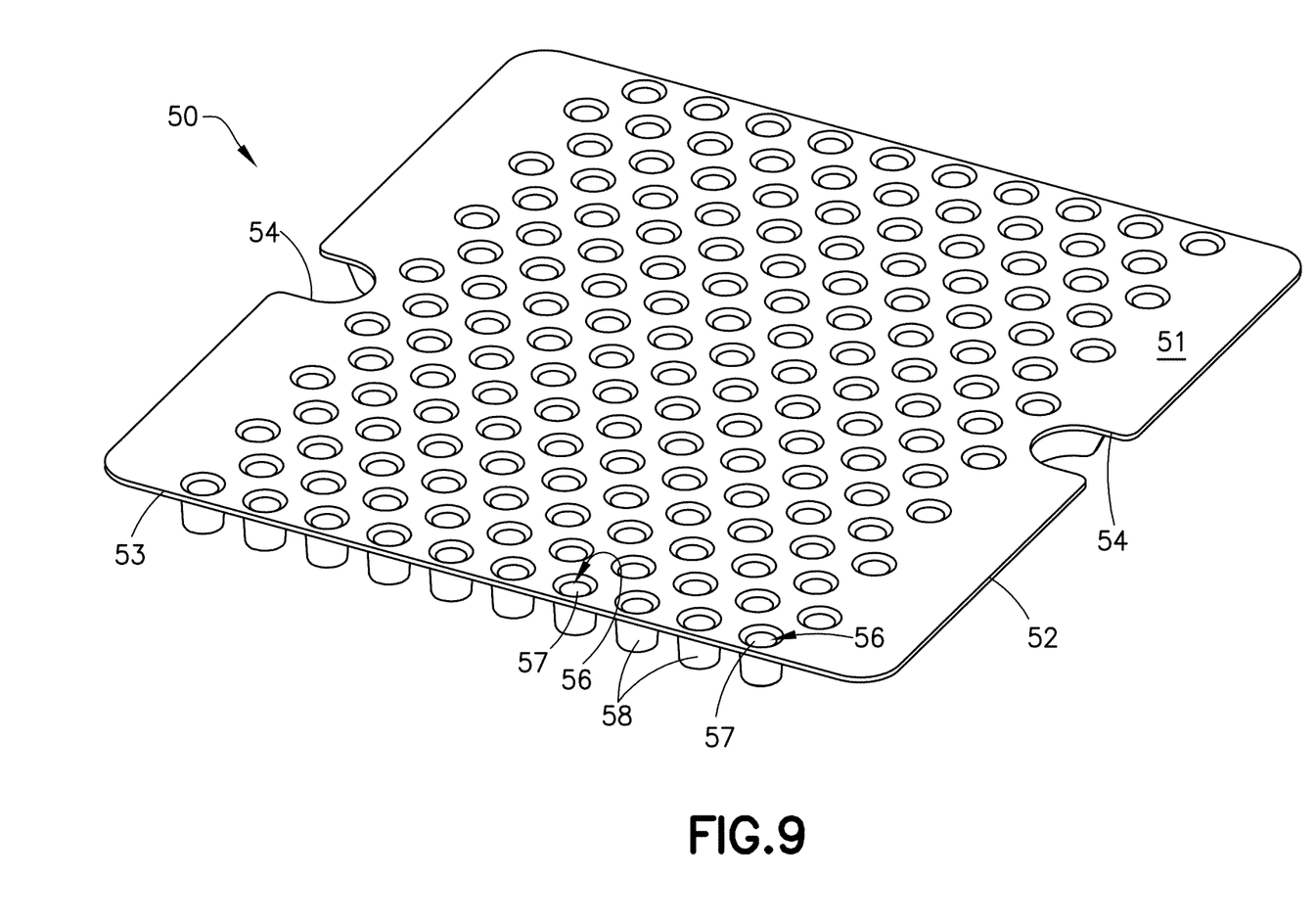
FIG. 9 is a top isometric view of a nest for the storage of plunger stoppers in accordance with another aspect of the present disclosure.
Figure 10:
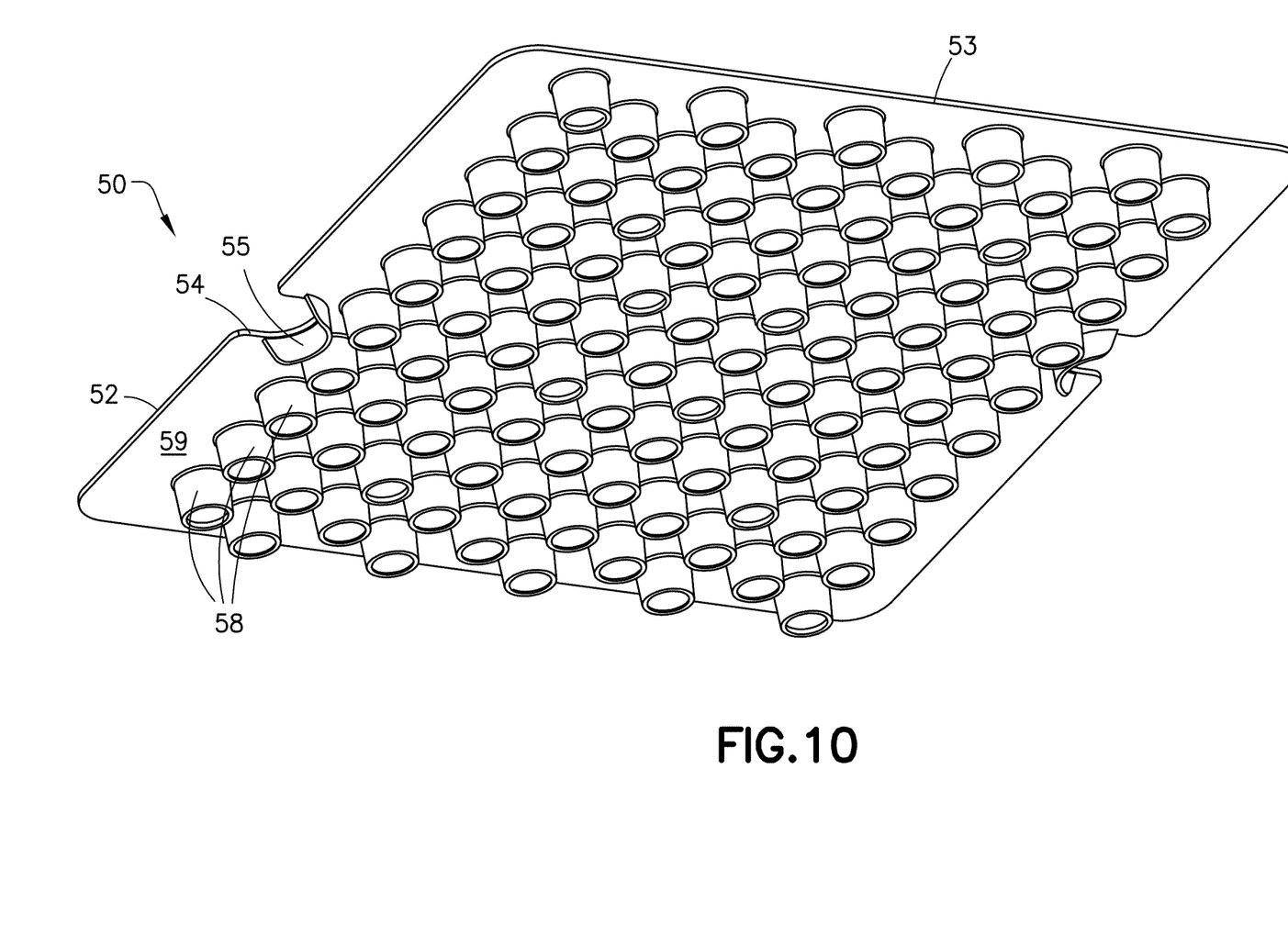
FIG. 10 is a bottom isometric view of the nest of FIG. 9.

As shown in FIGS. 9 and 10, the long sides 52 may each include a finger opening 54 formed thereon, wherein each finger opening 54 is designed to enable simplified manual loading (and/or removal) of the nest 50 into (or from), e.g., a tub or other holding arrangement. In some embodiments, a flange 55 may at least partially surround each finger opening 54 and extend from the bottom surface 59 of nest 50, thereby providing the user with a larger surface area upon which to grip the nest 50. While two finger openings 54 are shown on opposing long sides 52 in FIGS. 9 and 10, it is to be understood that nest 50 may include more or fewer finger openings, either on long sides 52 or the short sides 53. Additionally, in some embodiments, the finger openings 54 may be omitted altogether.

Unlike the use of ring-shaped protrusions to provide for alignment of stacked nests, nest 50 instead relies upon a plane 57 provided around the entry of each stopper receptacle 56. In particular, referring to FIG. 12, a cross-sectional view of a stopper receptacle 56 in accordance with an aspect of the present disclosure is shown. The plane 57 is formed as a substantially chamfered edge surface below the top surface 51 of the nest 50, adjacent the upper opening of stopper receptacle 56. The plane 57 may have a depth E and a width F. In one example, the depth E is about 0.5 mm and the width F is about 0.5 mm. However, it is to be understood that the plane 57 is not limited to these dimensions, and the depth E and width F may be larger or smaller, and need not necessarily be equal to one another.

Figures 11, 12:
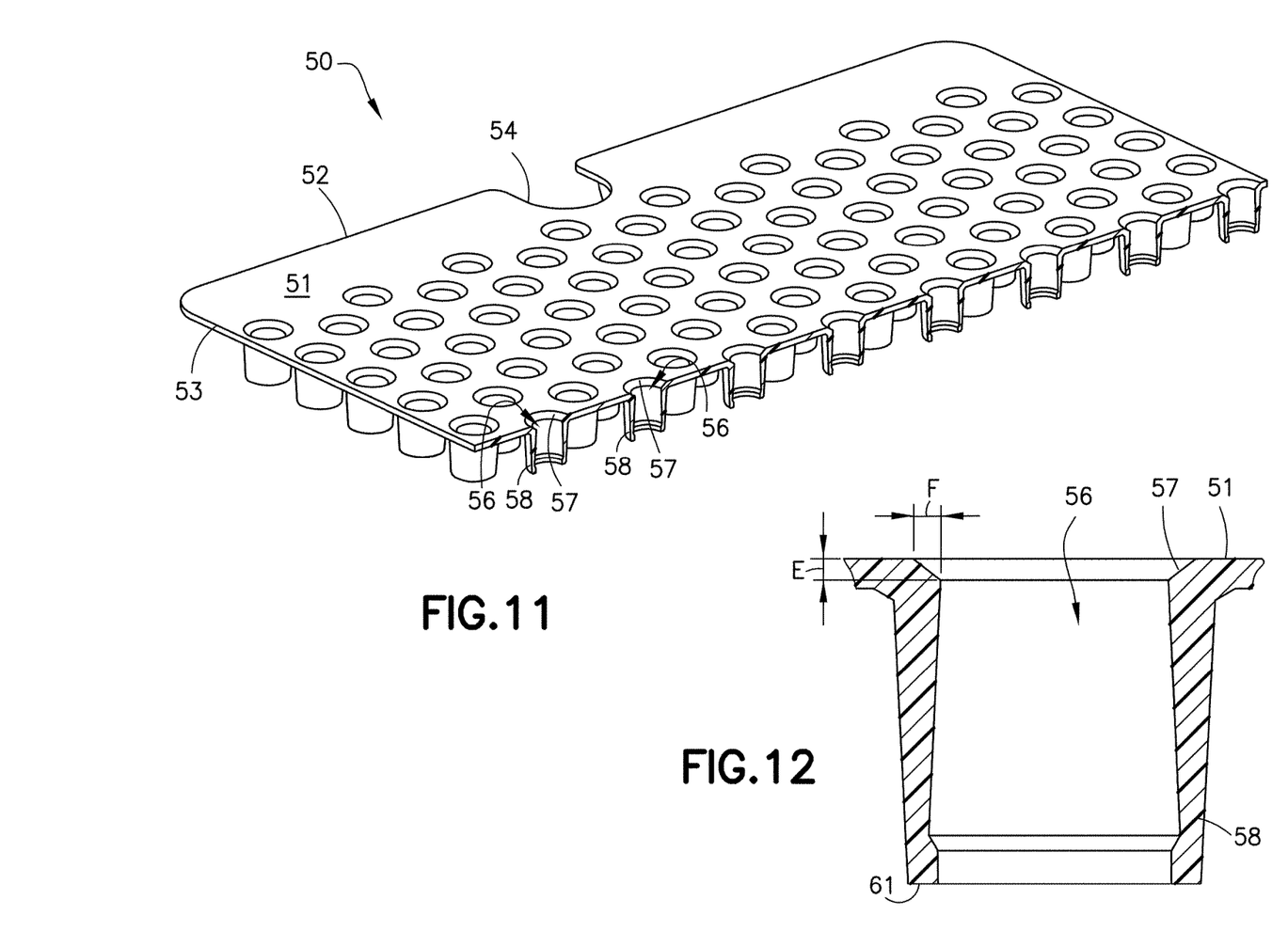
FIG. 11 is a cross-sectional isometric view of the nest of FIG. 9.
FIG. 12 is a cross-sectional side view of a stopper receptacle of the nest of FIG. 9.

The plane 57 is configured to provide for an inset support surface upon which a bottom surface 61 of a stopper receptacle 56 of a separate nest 50 may rest when one or more nests 50 are vertically stacked relative to one another. The plane 57 is sized and configured so as to substantially prevent easy dislodgement of adjacently stacked nests upon the application of minimal lateral force on a vertical stack of nests, while also absorbing both the nest's natural deformation and vertical movement due to, e.g., material properties, overall nest length and width, etc.

Each nest 50 may be formed of any suitable material, and via any suitable method. For example, nest 50 may be formed of, e.g., a plastic, polymer (e.g., polypropylene), metal, etc., and may be formed by, e.g., molding, stamping, extrusion, welding, etc. Furthermore, nest 50 may be formed as a single piece, or as multiple pieces coupled together. If formed of multiple pieces, the materials forming each piece may be the same or different.

Figure 13A:
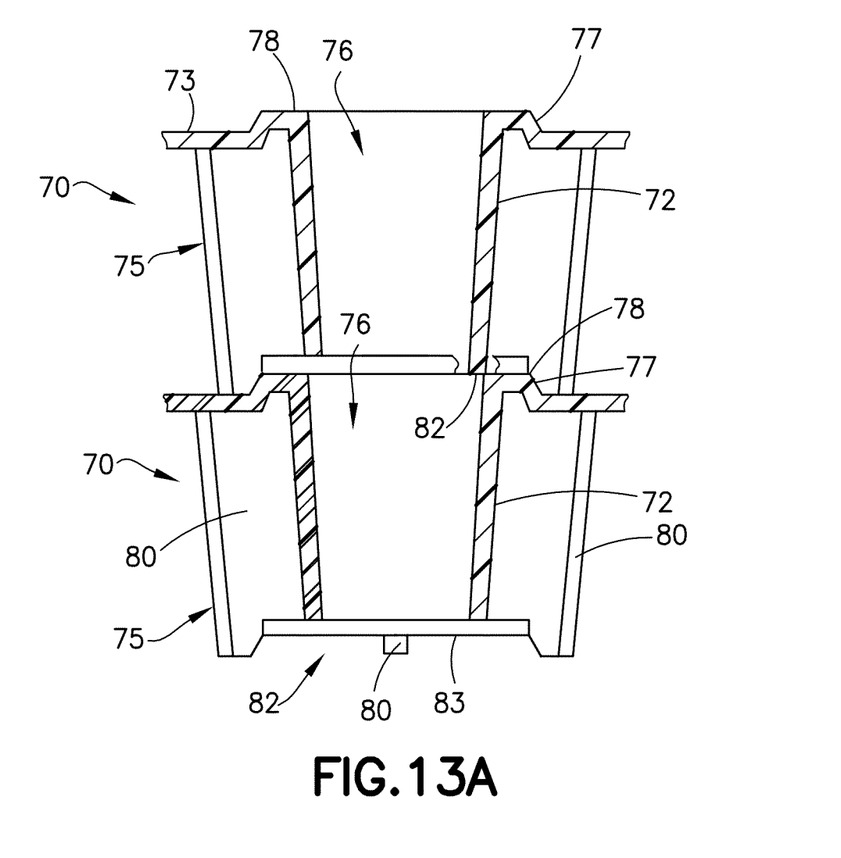
FIG. 13A is a cross-sectional side view of stacked stopper receptacles of respective nests in accordance with another aspect of the present disclosure.
Figure 13B:
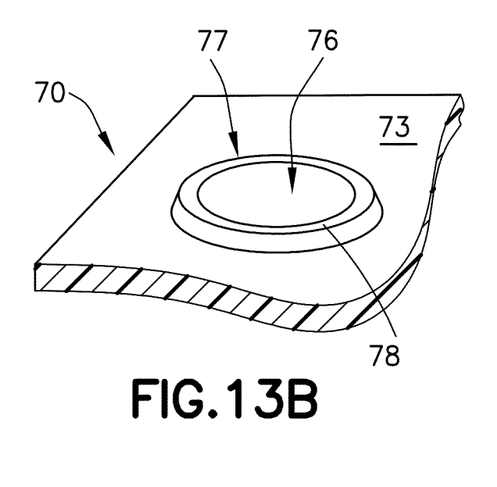
FIG. 13B is a partial top isometric view of a stopper receptacle and nest in accordance with another aspect of the present disclosure.

Referring now to FIGS. 13A-13B, a stopper receptacle 70 for use with a nest in accordance with another aspect of the present disclosure is shown. While not shown, it is to be understood that a plurality of stopper receptacles 70 are present in each nest, similar to those shown with respect to FIGS. 1-12.

FIG. 13A illustrates a pair of stopper receptacles 70 stacked atop one another, as would be the case when two nests are vertically stacked relative to one another. Each stopper receptacle 70 includes a substantially frustoconical sidewall portion 72 extending downward from a nest surface 73, with an opening 76 formed in each stopper receptacle 70 to receive, e.g., a plunger stopper (not shown). As shown in FIGS. 13A and 13B, a ring-shaped protrusion 77 extends upward from nest surface 73 and surrounds the opening 76, with each ring-shaped protrusion having a top surface 78.

Figure 13C:
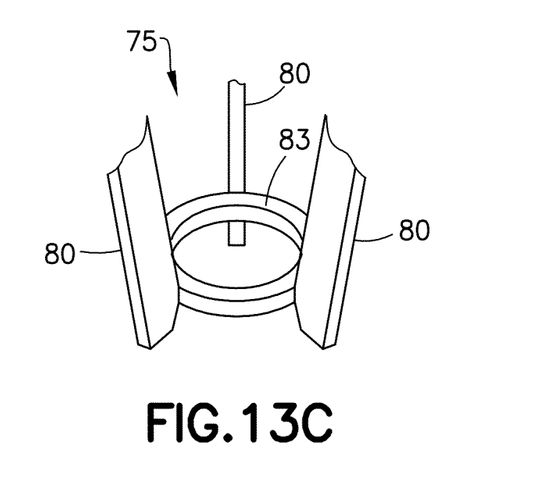
FIG. 13C is a top isometric view of leg portions configured to surround a stopper receptacle in accordance with another aspect of the present disclosure.

Furthermore, as shown in FIGS. 13A and 13C, a leg assembly 75 is provided, with the leg assembly configured around the frustoconical sidewall portion 72 of each stopper receptacle 70. In the embodiment shown, the leg assembly 75 includes three leg members 80, as well as a connecting ring 83 coupled to each of the leg members 80. However, it is to be understood that the leg assembly 75 may include more or fewer leg members 80. The leg members 80 are formed such that a bottom well portion 82 is formed below the connecting ring 83, providing for open space below the connecting ring 83. Furthermore, the leg assembly 75 may be integrally formed with the stopper receptacles 70 (by, e.g., molding), or the leg assembly 75 may be formed as one or more separate elements coupled to the stopper receptacles 70 by any appropriate method.

As can be seen in FIG. 13A, when the nests (and, thus, the stopper receptacles 70) are vertically stacked relative to one another, the bottom well portion 82 of the leg assembly 75 of an upper stopper receptacle 70 is sized and configured to substantially match the proportions of the ring-shaped protrusion 77. Thus, unlike the embodiments described with respect to FIGS. 1-12, where the stopper receptacle of the upper nest is supported within the stopper receptacle of the lower nest, the embodiment of FIGS. 13A-13B is configured such that the leg members 80 of the upper nest are positioned around the ring-shaped protrusion 77 of the lower nest. In some embodiments, the top surface 78 of the ring-shaped protrusion 77 may contact a bottom surface of the connecting ring 83. In this way, the internal diameter of the lower portion of leg assembly 75 substantially matches the external diameter of the ring-shaped protrusion 77, enabling the respective stopper receptacles 70 to be stacked securely relative to one another such that the stacked nests are consistently aligned and resist being dislodged by minimal lateral forces.

While several embodiments of nests and nest arrangements are shown in the accompanying figures and described hereinabove in detail, other embodiments will be apparent to, and readily made by, those skilled in the art without departing from the scope and spirit of the invention. For example, it is to be understood that this disclosure contemplates, to the extent possible, that one or more features of any embodiment can be combined with one or more features of any other embodiment. Accordingly, the foregoing description is intended to be illustrative rather than restrictive.

What is claimed is:

1. A nest for the storage of medical device components, comprising:
   a top surface,
   a bottom surface,
   a plurality of receptacles for the storage of a plurality of medical device components therein, wherein each of the plurality of receptacles comprises a sidewall portion extending downward from the bottom surface of the nest, and
   a plurality of ring-shaped protrusions extending upward from the top surface of the nest,
   wherein each of the plurality of ring-shaped protrusions is sized and configured to receive a bottom portion of a corresponding one of the plurality of receptacles when a plurality of nests are vertically stacked relative to one another, wherein the sidewall portion of a first set of the plurality of receptacles extends farther downward from the bottom surface of the nest than the sidewall portion of a second set of the plurality of receptacles, and wherein at least one receptacle of the plurality of receptacles is individually surrounded by a ring-shaped protrusion of the plurality of ring-shaped protrusions.

2. The nest according to claim 1, wherein each receptacle of the plurality of receptacles is individually surrounded by a respective ring-shaped protrusion of the plurality of ring-shaped protrusions.

3. The nest according to claim 1, wherein only some receptacles of the plurality of receptacles are individually surrounded by a respective ring-shaped protrusion of the plurality of ring-shaped protrusions.

4. The nest according to claim 1, wherein the plurality of receptacles are substantially frustoconical in shape.

5. The nest according to claim 1, further comprising a plurality of ledge portions, wherein an upper opening of each of the receptacles is individually surrounded by a respective ledge portion of the plurality of ledge portions.

6. The nest according to claim 5, wherein the ledge portion is sized so as to support a bottom surface of a respective one of the plurality of receptacles.

7. The nest according to claim 5, wherein a width of each ledge portion is about 1.5 mm.

8. The nest according to claim 1, wherein the height of each of the plurality of ring-shaped protrusions extending above the top surface of the nest is between 1.0-2.0 mm.

9. The nest according to claim 1, wherein an upper surface of each of the ring-shaped protrusions is rounded or chamfered.

10. The nest according to claim 1, wherein each of the plurality of receptacles having the sidewall portion which extends farther downward from the bottom surface of the nest than the sidewall portion of a second set of the plurality of receptacles is surrounded by one of the plurality of ring-shaped protrusions.

11. The nest according to claim 1, further comprising at least one finger opening formed therein.

12. The nest according to claim 11, further comprising a flange extending at least partially around each finger opening and extending from the bottom surface of the nest.

13. The nest according to claim 1, wherein the plurality of receptacles comprises between 100-160 receptacles.

14. The nest according to claim 1, wherein the nest is formed of polypropylene.

* * * * *

UNITED STATES PATENT AND TRADEMARK OFFICE
CERTIFICATE OF CORRECTION

PATENT NO. : 12,257,415 B2
APPLICATION NO. : 18/274086
DATED : March 25, 2025
INVENTOR(S) : Gildas Esnault et al.

Page 1 of 1

It is certified that error appears in the above-identified patent and that said Letters Patent is hereby corrected as shown below:

In the Specification

Column 1, Line 10, delete "fled" and insert -- filed --

Signed and Sealed this
Twenty-seventh Day of May, 2025

Coke Morgan Stewart
*Acting Director of the United States Patent and Trademark Office*